United States Patent [19]

Miyajima et al.

[11] Patent Number: 4,914,952
[45] Date of Patent: Apr. 10, 1990

[54] ULTRASONIC METHOD FOR MEASUREMENT OF SIZE OF ANY FLAW WITHIN SOLID MASS

[75] Inventors: Takeshi Miyajima; Yukio Ogura; Sadahisa Tomita, all of Ibaraki, Japan

[73] Assignee: Hitachi Construction Machinery, Co., Ltd., Tokyo, Japan

[21] Appl. No.: 215,752

[22] Filed: Jul. 6, 1988

Related U.S. Application Data

[63] Continuation-in-part of Ser. No. 57,896, Jul. 2, 1987, abandoned.

[51] Int. Cl.$^4$ .............................................. G01N 29/04
[52] U.S. Cl. ........................................ 73/598; 73/600
[58] Field of Search ................. 73/600, 627, 629, 598, 73/644

[56] References Cited

U.S. PATENT DOCUMENTS 3,608,361  9/1971  Krautkramer et al. ................ 73/629

FOREIGN PATENT DOCUMENTS 0207957  9/1987  Japan ..................................... 73/598

OTHER PUBLICATIONS

Krautkramer, J. et al., "Ultrasonic Testing of Materials", 2nd Edn., Sec. 5.1 (1977) pp. 90-96.

Primary Examiner—Stewart J. Levy
Assistant Examiner—Lawrence G. Fess
Attorney, Agent, or Firm—Wenderoth, Lind & Ponack

[57] ABSTRACT

The present invention provides an ultrasonic method for measuring the size of a possible flaw in a solid mass, in which an ultrasound is transmitted perpendicularly to the searching surface of a solid mass being the object under measurement through a liquid, a ratio in sound pressure between a reflected wave of the ultrasound from the surface of the solid mass and a reflected wave from any flaw in the solid, and a distance from the surface of the solid mass to the flaw, derived from the difference in time of reception between the reflected wave from the surface of the solid mass and the reflected wave from the flaw in the solid mass, are taken as indices of evaluation, and these indices of evaluation are compared with a reference value obtained beforehand by measuring a test piece made of a same material as that of the solid mass, thereby determining the size of the flaw. So, it is possible, with the present invention, to measure easily, very rapidly, accurately, quantitatively and non-destructively the size of a possible flaw in the parts or members composing any electrical or mechanical equipment.

1 Claim, 8 Drawing Sheets

ULTRASONIC METHOD FOR MEASUREMENT OF SIZE OF ANY FLAW WITHIN SOLID MASS

This application is a continuation-in-part of the U.S. application Ser. No. 057,896 filed on July 2, 1987 and now abandoned.

BACKGROUND OF THE INVENTION (a) Field of the Invention:

The present invention relates to an ultrasonic method for measurement of the size of any flaw possibly existent in various kinds of solid mass.

The term "solid mass" herein used refers to the parts or members of whatever the shape, dimensions or surface roughness, constituting, for example, an electrical, mechanical, chemical equipment or installation, etc. in various industrial fields. Further, the "solid masses" to which the present invention is applicable include a mass of a metal as well as a mass of a non-metal such as glass, ceramic, concrete, synthetic resin, rubber, wood, and the like through which the ultrasound wave can be propagated.

Also the size of a flaw possibly existent within a solid mass, referred to herein, points to that of a flaw of whatever the position, shape and kind found within the solid mass.

(b) Related Art Statement:

In the field of technique to which the present invention is applicable, it is very important and necessary to study, from the viewpoints of the strength and life of a piece of equipment or installation, the parts or members thereof for any flaw within it, and know, if any flaw is found within the part or member, what the flaw really is by measuring the position, shape and kind thereof and specifically the size thereof as well, thereby analyzing accurately the extent of adverse affect of the flaw to the part or member.

Such study is indispensable for essential parts or members. For this purpose, various techniques for radiographic tests utilizing radiations such as X-rays or gamma-rays as well as ultrasonic techniques have so far been employed for detection of any flaw.

By the technique for radiographic tests, an object is studied and analyzed for any internal flaw by observing an image produced with the radiation having been transmitted through the object, namely, by observing the change in the intensity of transmitted radiation which changes with the object shape, dimensions, material and the existence of any internal flaw. Therefore, the test results greatly depend upon the quality of the radiograph thus obtained. Since it is necessary to select a radiographic film of which the quality is suitable for radiography of an object to be tested and to do a series of photographic steps from radiography up to development, so the technique for the radiographic test is not simple and cannot be done easily and directly Also in some cases, if the film sensitivity and resolution are insufficient or even if they are not insufficient, the size of flaw cannot be measured and any flaw cannot even be detected; namely, in many cases, the technique for radiographic tests does not permit detection of what the flaw really is.

Also the ultrasonic pulse-echo techniques for detection of any internal flaw have been used from a long time. The typical and general one of such techniques is the direct-contact vertical flaw detection technique by which a vertical probe is applied in direct contact with the object (which will be referred to as "vertical flaw detection technique" hereinafter). Among the techniques of measuring the flaw size by the vertical flaw detection, three kinds of techniques are prevailing at present, including the utilization of (a) pulse-echo height; (b) probe directivity, and (c) ratio between F (flaw echo) and B (bottom echo).

Concerning the above-mentioned technique (a), the height of the echo appearing on the screen of an ultrasonic pulse echo flaw detector of A-scope display type (will be referred to as "ultrasonic flaw detector" hereinafter) depends upon the the roughness of the searching surface of an object under test, namely, the roughness of a surface upon which the ultrasonic wave is incident, attenuation of ultrasound being propagated, distance from the above-mentioned searching surface to a flaw possibly existent within the object and the size of the flaw when the total gain of the ultrasonic flaw detector is kept constant. Thus, the technique (a) is such that the object is compared with a comparison test piece prepared as reference test piece based on a known flaw size and the size of any flaw within the object is estimated through a sound field correction and a correction taking the shape or the like of the flaw in consideration. However, this technique is not highly reproducible as to the correction of sound field, flaw shape, and the like as the flaw size is larger, and also it is yet unclear in many points. So this technique is limited to the size measurement of small flaws of less than several millimeters. Also it is low in accuracy of measurement. Therefore, this technique cannot be widely adopted in measurement of flaw size.

The aforementioned technique (b) utilizes the directivity of the probe. Based on the fact that when the probe is displaced to a position where the center beam is off any flaw of a relatively large size, for example, a size larger than the transducer in the probe, the appearing flaw echo will be small, this technique makes it possible to know the flaw size from the range in which no flaw echo appears. However, this technique cannot provide accurate measurement of flaw size because of the interaction among various factors such as the uncertain directivity of reflection, requirement for sufficient distance of flaw position from the searching surface, attenuation of ultrasound, nonlinear beam propagation, etc.

Figure 10:
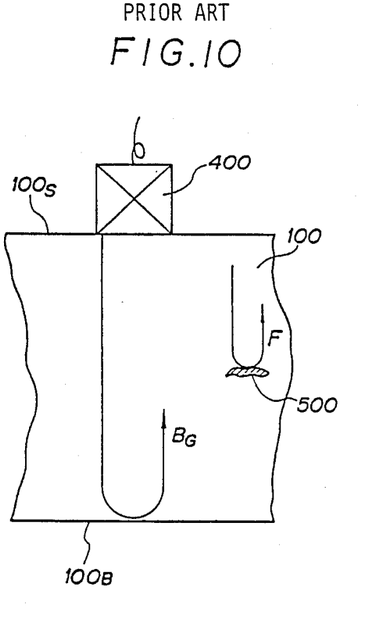
FIG. 10 is an explanatory drawing showing the principle of the F/BG method being a conventional method of flaw detection.
Figure 11:
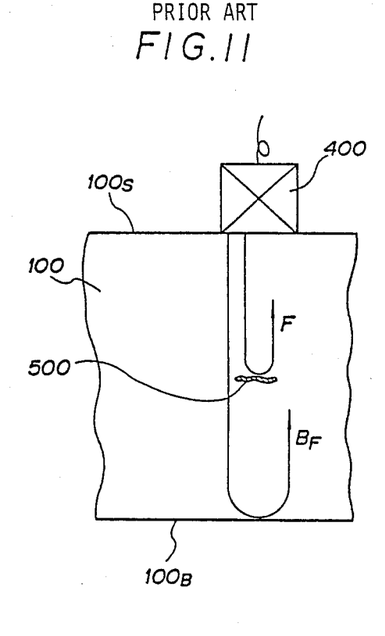
FIG. 11 is also a drawing explaining the principle of the conventional F/BF method.

The technique (c) mentioned above further includes two techniques: F/BG method and F/BF method. The former method F/BG utilizes the ratio between the height of the maximum echo from a flaw 500 (will be referred to as "F echo" hereinafter) to that of the echo of a sound pressure B from the bottom surface 100B of a whole region in which there is not the flaw 500 (which will be referred to as "BG echo" hereinafter) as shown in FIG. 10. As shown in FIG. 11, the F/BF method utilizes the ratio of the height of the F echo to that of the F echo of a sound pressure F from the flaw 500 (which will be referred to as "BF echo" hereinafter).

In the F/BG method, when the shape and the surface roughness of the bottom surface 100B of an object 100 which provides the BG echo are similar to those of the standard or comparison test piece and the flaw size is rather small as compared with the transducer size, the flaw size is quantitatively evaluated to some extent with an expression, for example, "it is approximate to STB-G, V15-4" or "it is on the order of 6 mm as converted into a circular flat flaw using the AVG diagram.

On the other hand, since the F echo detecting position is the same as the BF echo detecting position, the F/BF method is not so much affected by the shape and roughness of the searching surface 100S and the accuracy of flaw detection does not greatly depend upon such factors. Furthermore, this method is practically advantageous in that the reduction of the BF echo height due to the existence of a flaw 500, namely, the shadow effect of the flaw 500, can also be evaluated. Since this shadow effect occurs due only to the size of the flaw 500, not to the shape thereof, so any large flaw will lead to the reduction of BF echo height. Therefore, a flaw of a large size (but smaller than the size of the transducer) can be evaluated with a higher accuracy by the F/BF method through the evaluation of the F echo. However, both these F/BG and F/BF methods are not advantageous and have the problems as will be described:

(1) First, since the ratio between F and BG echoes, or the ratio between the F and BF echoes, is taken as index of evaluation, the reflectance of the bottom surface which is likely to be affected by the shape, inclination and roughness of an object under inspection should be constant.

(2) For the BG and BF echoes, the bottom surface 100B must be smooth and have an effective area of reflection, and any object of a shape and size that could not provide the BG and BF echoes cannot be measured by these methods.

(3) In case an object of which the searching surface 100S is rough such as cast surface, shot-blasted surface, etc. is measured, it is necessary to use an acoustic contact medium between the searching surface 100S and probe 400. However, even if a contact medium suitable for the shape and inclination of the searching surface 100S is selected for this purpose, air or bubble is likely to exist in the medium and degrade the ultrasound transfer characteristic of the medium, which will cause the echo height to vary. Thus, it is not possible to measure with a high accuracy.

(4) These methods need a searching surface 100S of an area which enables the probe 400 to be in contact therewith. Any object having only a narrow surface on which the probe 400 cannot be applied cannot be measured for any flaw by these methods.

(5) In case of the F/BF method, there is no correlation between the F echo height and the size of a flaw which is larger than that of the transducer, and the ultrasound will not arrive at the bottom surface 100B of the object in which the flaw exists, so that no BF echo can be obtained. So in such case, no flaw size measurement can be done by this method.

(6) In both these methods, the equation for determining the flaw size is a quartic one of which the solution takes much time.

The methods of flow detection that overcome these problems to some extent include a water or oil immersion method (will be referred to as "liquid immersion method" hereinafter). In this method, an entire object is immersed in a liquid or only the liquid is locally filled only between the probe and object, and ultrasound is transmitted through the liquid toward the searching surface from the probe located at a position of some distance from the searching surface of the object. However, this method can generally solve only the above problems (3) "the accuracy of flaw size measurement is affected by the roughness of the searching surface" and (4) "a searching surface of such a sufficient area that the probe can be applied to the object", but not the practical problems in the flaw size measurement which have been a large difficulty in the measurement of flaw size.

As has been described in the foregoing, a large quantity of objects cannot be measured directly along the production line, in other words, they cannot be measured in a short time, with a high accuracy and quantitatively, by these conventional methods.

Also, when a flaw detection is done by scanning with the probe being moved as kept applied on the surface of the object, the sound pressure of the reflected echo from a flaw varies depending upon the contact pressure of the probe and the inclination of the probe with respect to the object. The method of compensating this gain variation is disclosed in the Japanese Unexamined Patent Publication (Kokai) No. 58-68663. This method utilizes the fact that the sound pressure of the reflective wave from the surface of the object in proportion to the variation in sound pressure of the flaw-reflected wave depending upon the condition of contact of the probe on the object. The above-mentioned Unexamined Patent Publication discloses a concept that the value of the ratio $h_{S/F}$ between the echoes S and F is constant independently of the conditions of ultrasound incidence from the probe. In this case, even if the amplitude of the echo from any flaw is only compensated, the size of the flaw cannot be measured. It is necessary to take in consider the relation between the size of the flaw and the location of the flaw.

SUMMARY OF THE INVENTION

The present invention basically seeks to overcome the aforementioned drawbacks of the conventional techniques by providing an ultrasonic method for measurement of the size of any flaw in a solid mass easily, rapidly, accurately and quantitatively without being influenced by the roughness, shape, inclination and area of the searching and bottom surfaces.

The present invention also seeks to provide a method of automatically inspecting a large quantity of objects along the production line to detect any flaw within the solid mass thereof and measure the size of the flaw.

The above objects of the present invention are attained by providing an ultrasonic method for measurement of the size of any flaw, in which an ultrasound is transmitted perpendicularly to the searching surface of a solid mass being the object under measurement through a liquid, a ratio in sound pressure between a reflected wave of the ultrasound from the surface of the solid mass and a reflected wave from any flaw in the solid, and a distance from the surface of the solid mass to the flaw, derived from the difference in time of reception between the reflected wave from the surface of the solid mass and the reflected wave from the flaw in the solid mass, are taken as indices of evaluation, and these indices of evaluation are compared with a reference value obtained beforehand by measuring a test piece made of a same material as that of the solid mass, thereby determining the size of the flaw.

More particularly, the present invention utilizes the following property of the ultrasound. That is say, when an ultrasound is emitted from a probe wholly immersed in a liquid perpendicularly toward the searching surface of a solid mass which is also wholly immersed in the liquid and the surface-reflected wave of the ultrasound from the searching surface of the solid mass and the flaw-reflected wave are received by the probe, there is a fixed correlation between the result of a comparison between the sound pressure of the aforementioned surface-reflected wave and that of the flaw-reflected wave, and the distance from the searching surface of the solid mass to the flaw and the size of the flaw.

This will be explained in detail with reference to FIGS. 1 and 2 which illustrate the principle of the present invention.

Figure 1:
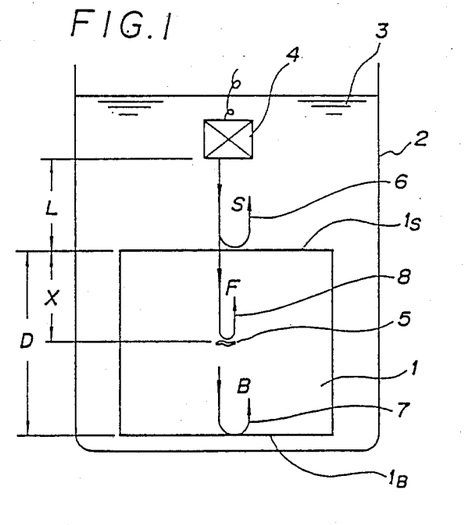
FIG. 1 is a drawing explanative of the basic principle of the ultrasonic method for measurement of the size of any flaw in a solid mass according to the present invention.
Figure 2:
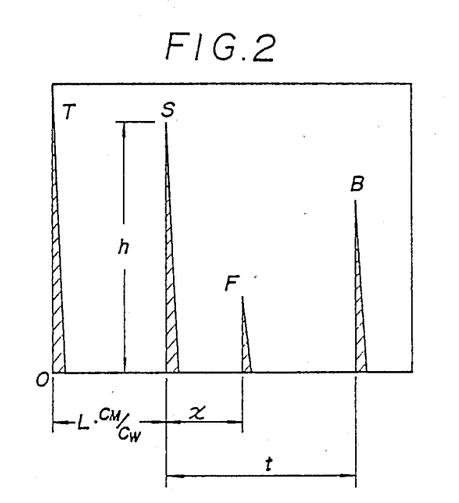
FIG. 2 is an explanatory drawing of the echo pattern displayed on a CRT, obtained by the method shown in FIG. 1.

FIGS. 1 and 2 show both the inventive method and the conventional method of flaw detection and the echo pattern in the method, respectively. As has been described in the foregoing, the present invention utilizes the ratio in sound pressure between the surface-reflected wave and flaw-reflected wave. So the present invention will be explained with reference to these Figures which are illustrated as simplified for better understanding of the present invention.

In FIG. 1, the reference numeral 1 indicates an object under inspection which is immersed in a liquid 3 such as water or oil (water in this description) in a bath 2. The numeral 4 indicates a vertical probe for water-immersion use which is immersed along with the object 1 in the water 3 in the bath 2.

The probe 4 is so held by a support (not shown) that it emits ultrasound generally perpendicularly toward the searching surface 1S of the object 1. The ultrasound emitted from the probe 4 nearly perpendicularly toward the searching surface travels through the water 3 and arrives at the searching surface 1S. The ultrasound is reflected by the searching surface 1S with a reflectance partially depending upon the distance L between the probe 4 and searching surface 1S but nearly totally based on the difference in acoustic impedance between the object 1 and water 3, and it is partially received by the probe 4 as a reflected wave 6 of a sound pressure S. The other part of the ultrasound penetrates into the object 1, and in case there exists no flaw within the object 1, the ultrasound goes to the bottom surface 1B of the object 1 and is reflected by the bottom surface 1B after arriving there. This ultrasound is received by the probe 4 as a bottom-reflected wave 7 of a sound pressure B. However, if any flaw 5 exists within the object 1, a reflected wave 8 of a sound pressure F from the flaw 5 and the reflected wave 6 and bottom-reflected wave 7 as well are received by the probe 4. When displayed on a CRT screen of A-scope display, these sound pressure signals yield an echo pattern as shown in FIG. 2. That is, a transmitted pulse of ultrasound T is displayed at the position of the origin 0 of the CRT time base, the echo S of the reflected wave 6 is displayed at a position of a product L·CM/CW of the distance L from the position of the transmitted ultrasound pulse T, speed CW of the ultrasound in the water 3 and the speed CM of th ultrasound inside the object 1, the echo F of the flaw-reflected wave 8 is displayed at a position delayed a time x equivalent to the distance between the searching surface 1S and flaw 5, namely, the depth of flaw X, from the position of the echo S, and the echo B of the bottom-reflected wave 7 is displayed at a position delayed a time t equivalent to the thickness D of the object 1 from the position of the echo S. They are all displayed at the same time. The reflected waves 6, 7 and 8 obtained by effecting the immersion method shown in FIG. 1 are displayed as the echo pattern on the CRT as shown in FIG. 2 to detect any flaw within the object.

The method of flaw detection having been described above is partly similar to the conventional method utilizing the parameters (a), (b), and (c) described in the "BACKGROUND OF THE INVENTION", i.e. similar in utilizing the reflected wave and the echo pattern; however, various problems or drawbacks in the conventional method which have been described previously have been overcome by the inventive method of flaw detection.

However, the method of flaw detection according to the present invention is quite different from the aforementioned conventional technique in the following respects. Namely, a ratio F/S in sound pressure between a reflected wave 8 from a flaw 5 and a reflected wave 6 from the searching surface 1S of the object 1S that is obtained by the conventional method, and a distance, namely, a depth X of flaw, from the searching surface 1S to the flaw 5, calculated from a difference x in time of reception between the reflected wave 6 from the searching surface 1S and reflected wave 8 from the flaw 5, that is obtained by the conventional method, are taken as indices of evaluation and are compared with the reference value previously obtained using test pieces made of a same material as the object 1, thereby determining the size of the flaw 5. As the ratio in sound pressure F/S between the reflected waves 8 and 6, the value of $h_{F/S} = 20 \log F/S$ is used which is a presentation in dB of the echo height ratio being a comparison value between echoes F and S shown in FIG. 2. As the reference value determined previously using a test piece of a same material as the object 1, the a value derived from a correlation between the value of the echo height ratio $h_{F/S}$, depth X and size of the flaw is used. Thus, the influence of various factors being the problems in the conventional method of flaw detection can be all eliminated. Also the values $h_{F/S}$, x and t can be displayed on the CRT and can be easily determined. So the size of the flaw within the object can be measured easily, rapidly, accurately, and quantitatively from the correlation between the value of $h_{F/S}$ and the depth and size of the flaw, and also a large quantity of objects can be detected for any flaw easily and automatically.

Since the method of flaw detection according to the present invention utilizes the sound pressure ratio between the reflected wave from the searching surface of the object and the reflected wave from the flaw, the result of flaw detection is constant without being affected by the surface roughness. This will be proved below using the results of the Inventor's experiments.

Figure 3:
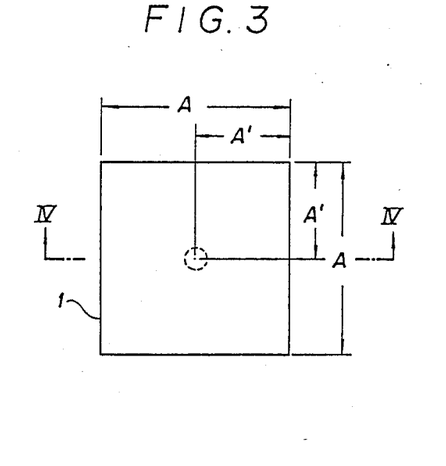
FIG. 3 is a plan view of the object used to prove the present invention.
Figure 4:
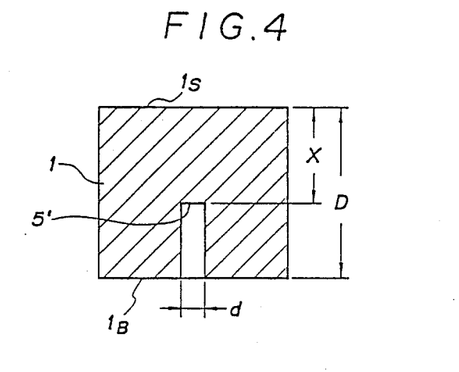
FIG. 4 is a sectional view taken along the line IV—IV in FIG. 3.
Figure 5:
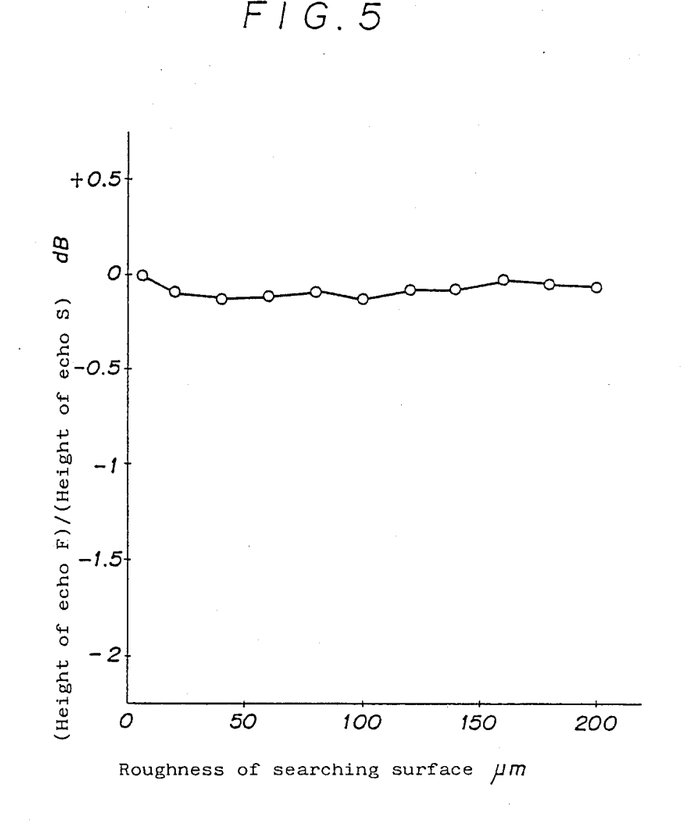
FIG. 5 graphically shows the relation between the roughness of the searching surface and change in value of the ratio between the flaw echo F and searching-surface echo S.

The object 1 used in the experiment has a square shape as shown in FIGS. 3 and 4 of which the length A is 100 mm, length A' is 50 mm and the thickness D is 50 mm. The object 1 has formed at the center of the bottom surface 1B thereof a round flat-bottomed hole of which the diameter d is 2 mm, and the distance from the searching surface 1S to the flat bottom surface 5' of the hole, namely, the depth of flaw, is 15 mm. The material of the object 1 is FCD45 (spherical graphite cast iron according to JIS G5502). Eleven kinds of surface roughness of the searching surface 1S were prepared in a range from 6 μm to 200 μm (with increments of 20 μm) in 10-point mean roughness (according to JIS B0601). The sound pressure was measured as 0 dB in case of the accuracy of finish being 6 μm. The probe frequency was 5 MHz. The results of measurements are shown in FIG. 5. In this Figure, the vertical axis takes the ratio in height between echoes F and S in decibel, while the horizontal axis takes the roughness of the searching surface 1S (10-point mean roughness in m). As apparent from FIG. 5, even when the accuracy of finish is on the order of 200 μm approximate to those of the cast surface and shot blasted surface, the height ratio between the echoes F and S remains little changed. This proves that when the F/S value is taken as index of evaluation, the method of flaw detection according to the present invention is not affected by the roughness of searching surface.

The present invention is based on the finding that the amplitude of the echo F varies depending upon the distance from the surface to the flaw, that is, the flaw depth X and flaw size d, namely, these factors are in a certain relation among them. It is well known that when the flaw size is larger, the echo F is also larger, or that when the flaw depth X is large, the ultrasound is attenuated and the echo F is smaller. The extent of the ultrasound attenuation does not vary only depending upon the distance x but upon the flaw size d. Assume that the relation between the ratio $h_{F/S}$ between the echoes F and S and the flaw depth X is as follows:

$$h_{F/S} = -a \log X - b \quad (1)$$

where
 a: constant of proportion
 b: constant

The relation among these constants a and b and the flaw size d can be expressed as follows:

$$a = 10^{-a1 \log d + b1} \quad (2)$$

$$b = 10^{-a2 \log d + b2} \quad (3)$$

The terms a1, b1, a2 and b2 are constants in the above equations. By determining the values of these constants through measurement of a test piece of a same material as an object to be measured, the flaw size d can be determined from the values of $h_{F/S}$ and X using these equations. By substituting the equations (2) and (3) into the equation (1), the following general equation is obtained:

$$h_{F/S} = -10^{-a1 \log d + b1} \cdot \log X - 10^{-a2 \log d + 2} \quad (4)$$

Because the method of flaw detection according to the present invention is characterized in that it is not affected at all by the shape, dimensions and roughness of the bottom surface of the object, the values $h_{F/S}$ and x displayed on the CRT are utilized and that it is little influenced by the roughness of the searching surface, the present invention can attain a high accuracy and quantitativeness, which could not be realized with the conventional techniques, of the detection of any bubble mixed in, cavity (or blow-hole) formed in and segragation in iron castings, steel castings, etc. of which the surfaces are rough, any sand mark, sand inclusion, fissure, etc. in the steel forgings, and any segregation, crack, and the like in the tubings.

The correlation between the values hF/S, X and flaw size will be described in further detail referring to the embodiment of the present invention.

These and other objects and advantages of the present invention will be better understood from the ensuing description made, by way of example, of the embodiment of the present invention with reference to the drawings

DETAILED DESCRIPTION OF THE PREFERRED EMBODIMENTS

Referring now to FIGS. 2 to 4 and 6 to 9, the preferred embodiment of the present invention will be described hereafter.

Figure 6:
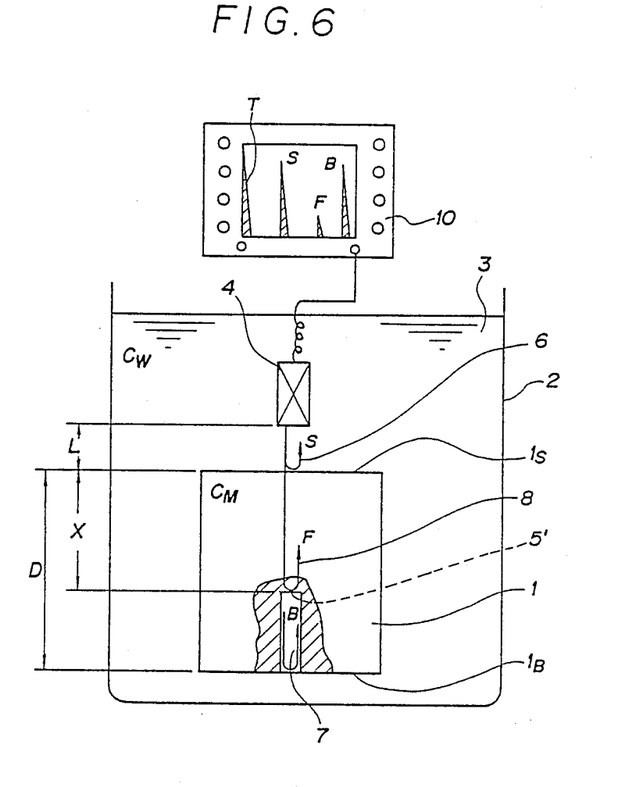
FIG. 6 is a schematic explanatory drawing showing an embodiment of the present invention.

In FIG. 6, the reference numeral 1 indicates an object prepared like the sensitivity standard test piece, and it is immersed in the water 3 in the bath 2. The object 1 has a same shape and outside dimensions as those shown in FIGS. 3 and 4, and it is a square thick plate of which the thickness D 50 mm and the length of one side A=100 mm. The object 1 has a round flat-bottomed hole formed in the center of the bottom surface 1B thereof. Objects are prepared as follows: They are provided with three kinds of flat-bottomed hole diameters d being φ2, φ4 and φ6, respectively, and also with eleven kinds of distance from the searching surface 1S to the flat bottom surface 5' of the hole, namely, flaw depth X, being 5, 6, 8, 10, 15, 20, 25, 30, 35, 40 and 50 mm for each of the diameter d of the flat-bottomed hole.

The accuracy of finish of the object 1 is a 10-point mean roughness of about 6 μm to 15 μm (according to JIS B0601). The material of the object 1 is a spherical graphite cast iron FCD45 (according to JIS G5502). The numeral 4 is an immersion type probe, and it is also immersed in the water 3 in the bath 2. The probe 4 is held by a sufficiently rigid support (not shown) in such a manner that the ultrasound is emitted from a position of a distance L=100 mm nearly perpendicularly toward the searching surface 1S of the object 1. Also the probe is so held that it can be moved in directions perpendicular to each other in a plane parallel to the searching surface 1S without changing the angle with respect to the object 1 and that the angle can be fine-adjusted. The water 3 is not any fresh one; the water is heated to a temperature of 60° to 70° C. once to expel the oversaturated air from the water and then cooled before used, thereby preventing the reduction of the sensitivity of reception (gain). The probe 4 is of 5 MHz in frequency and has a transducer made of a porcelain of zirconium lead titanate (5Z10i according to JIS Z2344) and of which the diameter is 10 mm. The probe 4 is connected to an ultrasonic flaw detector 10 by means of a high frequency cable.

Figure 7:
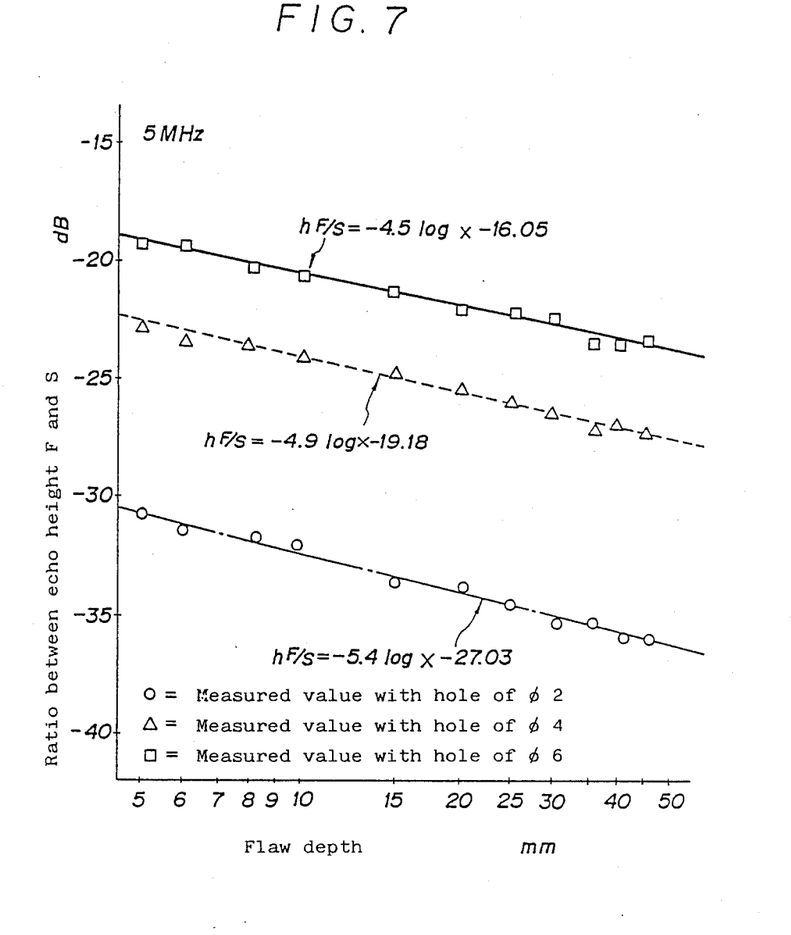
FIG. 7 is a graph of the correlation between the flaw depth and the difference in height of the F/S echo, which is obtained by the method shown in FIG. 6.

The probe 4 emits ultrasound toward the searching surface 1S. A part of the ultrasound is reflected at the searching surface 1S to be a reflected wave of a sound pressure F. The other part of the ultrasound penetrates into the object 1 and reaches the flat bottom surface 5'. Then it is partially reflected there to be a reflected wave 8 of a sound pressure S. The other part of the ultrasound further travels and reaches the bottom surface 1B, and is reflected there to be a bottom-reflected wave 7 of a sound pressure B. These reflected waves 6, 7 and 8 are received by the probe 4 and then displayed as echoes S, F and B along with the transmitted pulse T in the order of T, S, F and B on the CRT of the ultrasonic flaw detector 10. These pulse and echoes form the echo pattern as having been described with reference to FIG. 2. The ratio in height between the echoes F and S displayed on the CRT is determined for each of the aforementioned kinds of objects, and the results are shown in FIG. 7. The vertical axis of the graph in FIG. 7 shows the value $h_{F/S}$ in dB of the height ratio between the echoes F and S, while the horizontal axis takes the logarithmic value of the distance from the searching surface 1S to the flat bottom surface 5', namely, the flaw depth X (in mm). The parameter is the diameter d of the flat-bottomed hole, and the measured values with the hole of $\phi 2$ in diameter, with $\phi 4$ and with $\phi 6$ are plotted with marks of o, $\triangle$ and $\square$, respectively. The graph in FIG. 7 clearly shows that there is a linear correlation between the value $h_{F/S}$ and the flaw depth X.

By using the above-mentioned measured values in the reggression equation (1) and solving the equation by the method of least squares for the diameter d of each flat-bottomed hole, the following results:

| Diameter d of flat-bottomed hole | Regression equation |
|---|---|
| $\phi 2$ mm | $h_{F/S} = -5.4 \log X - 27.03$ |
| $\phi 4$ mm | $h_{F/S} = -4.9 \log X - 19.18$ |
| $\phi 6$ mm | $h_{F/S} = -4.5 \log X - 16.05$ |

Figure 8:
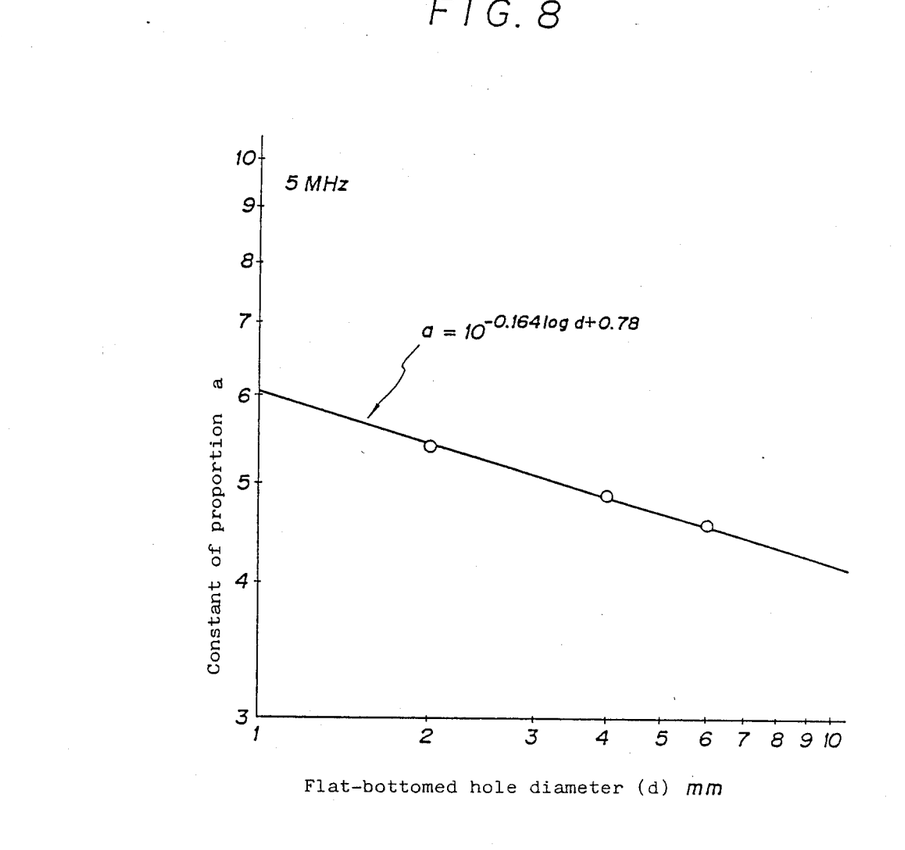
FIG. 8 shows the correlation between the diameter d of the flat-bottomed hole formed in the object and the constant of proportion a indicating the gradient of regression equation.

Next, by relating the constant of proportion a (a in the equation (1)) in each of the regression equations in the above Table with the diameter d of the flat-bottomed hole, the graph shown in FIG. 8 is obtained. The vertical axis of this graph takes the logarithmic value of the constant of proportion a, while the horizontal axis shows the diameter d (in mm) of the flat-bottomed hole in logarithmic value. Also in FIG. 8, there is established a linear correlation between both these parameters; namely, the larger the diameter d of the flat-bottomed hole, the smaller the value of the constant of proportion a becomes. By solving this regression equation by the method of least squares, the following results:

$$a = 10^{-0.164 \log d + 0.78} \tag{5}$$

Figure 9:
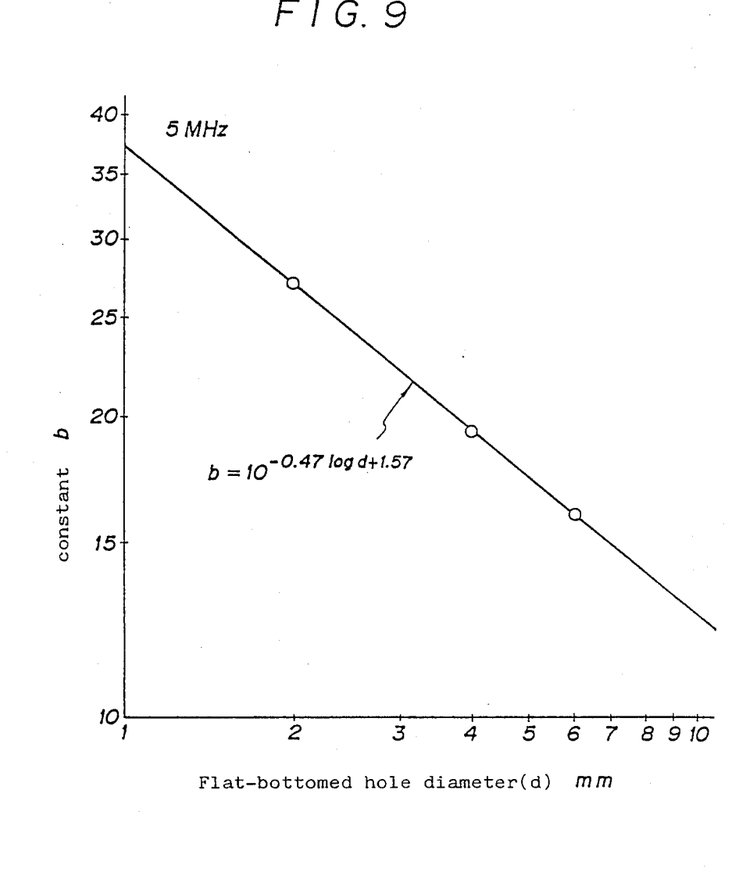
FIG. 9 shows the correlation between the diameter d of the flat-bottomed hole formed in the object and the constant b of the regression equation.

On the other hand, by relating the constant b (b in the equation (1)) of each of the regression equations in the above table with the diameter d of the flat-bottomed hole, the graph shown in FIG. 9 is obtained. In this graph, the vertical axis takes the logarithmic value of the constant b, while the horizontal axis shows the logarithmic value of the diameter d (in mm) of the flat-bottomed hole. Also this graph suggests that there is a linear correlation between both these parameters; the larger the diameter d of the flat-bottomed hole, the smaller the value of the constant b becomes. By solving this regression equation by the method of least squares, the following results:

$$b = 10^{-0.47 \log d + 1.57} \tag{6}$$

By substituting the equations (5) and (6) into equation (1), the following is obtained:

$$h_{F/S} = -10^{-0.164 \log d + 0.78} \cdot \log X - 10^{-0.47 \log d + 1.57} \tag{7}$$

If the value of $h_{F/S}$ and flaw depth are known from the equation (7), the size of the diameter d of the flat-bottomed hole will be quantitatively known. Since the value of $h_{F/S}$ and the value of flaw depth X can be simply and easily known from the height ratio between the echoes F and S and the delay time x of the time base displayed on the CRT of the ultrasonic flaw detector, the size of the flaw can be known rapidly, easily, accurately and quantitatively.

The constant of proportion a and the constant b in the equation (1) are determined by the acoustic characteristic of the material of the object. By determining such constants concerning various kinds of solid mass by experiments, the size of flaw can be known extremely simply and easily as in the embodiment having been described in the foregoing.

As has been described in the foregoing, the ultrasonic method for measurement of the size of any flaw within a solid mass is such that ultrasound echoes are displayed on CRT and the size is visually known from the echo pattern formed with the echoes. However, it is also possible to digitize the analog quantities of the echo height and the flaw detecting distance along the time base by means of a conventional means, and calculate these analog quantities using a relational expression correlated with the size of flaw, thereby digitally indicating these values along with the flaw size. Furthermore, it is possible to store such values in a memory for comparison with reference ones, whereby any equipment can be diagnosed for, and prevented against, any fault or trouble and a large quantity of objects can be easily inspected for any flaw or defect by means of the automatic flaw detection along the production line.

As apparent to those skilled in the art, the present invention is not limited only to the embodiment having been described in the foregoing, but it can be embodied in various manners without departing from the spirit and scope of the present invention.

What is claimed is:

1. A method for measuring a size of any flaw with ultrasonic waves wherein the ultrasonic waves are transmitted perpendicularly to a searching surface of a solid mass being the object under measurement through a liquid, comprising the following steps of:
   detecting the echo height of a first reflected wave from the searching surface of the solid mass and that of a second reflected wave from the flaw in the solid mass, respectively, to obtain a ratio in echo height between said first and second reflected waves;
   detecting the difference in propagation time between said first and second reflected waves, to obtain the depth of the flaw from the solid-mass surface, which corresponds to the detected difference; and determining the size of the flaw from the obtained echo-height ratio and the obtained flaw depth based on a predetermined correlation among the echo-height ratio between the first and second reflected waves, the depth of the flaw from the solid-mass surface, and the size of the flaw, the predetermined correlation being pre-established from standard test pieces of the same material as the material of the solid mass under measurement, wherein the predetermined correlation is expressed as follows:

$$hF/s = -10^{-a1\ \log d + b1} \log X - 10^{-a2\ \log d + b2}$$

where
 hF/S: ratio in echo height between the first and second reflected waves,
 X: depth of the flaw from the solid-mass surface,
 d: size of the flaw, and
 a1, a2, b1, and b2: constants, said predetermined correlation being obtained by determining the constants a1, a2, b1, and b2 beforehand using standard test pieces of the same material as the material of the solid mass under measurement and having different flaw sizes.

* * * * *